US009945871B2

(12) United States Patent
Martinez et al.

(10) Patent No.: US 9,945,871 B2
(45) Date of Patent: Apr. 17, 2018

(54) METHOD FOR MEASURING THE LEVEL OF CIRCULATING INHIBITORY FACTOR 1 PROTEIN IN A SUBJECT MEASURING THE LEVEL OF CIRCULATING INHIBITORY FACTOR 1 (IF1) PROTEIN IN A SUBJECT

(71) Applicants: Laurent Martinez, Toulouse (FR);
Bertrand Perret, Toulouse (FR);
Annelise Genoux, Toulouse (FR)

(72) Inventors: Laurent Martinez, Toulouse (FR);
Bertrand Perret, Toulouse (FR);
Annelise Genoux, Toulouse (FR)

(73) Assignees: INSERM (INSTITUT NATIONAL DE LA SANTE ET DE LA RECHERCHE MEDICALE, Paris (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 50 days.

(21) Appl. No.: 14/694,249

(22) Filed: Apr. 23, 2015

(65) Prior Publication Data
US 2015/0226749 A1 Aug. 13, 2015

Related U.S. Application Data

(63) Continuation of application No. 13/981,666, filed as application No. PCT/EP2012/051080 on Jan. 25, 2012, now Pat. No. 9,052,326.

(60) Provisional application No. 61/436,239, filed on Jan. 26, 2011.

(30) Foreign Application Priority Data

Jan. 26, 2011 (EP) ..................................... 11305080

(51) Int. Cl.
*G01N 33/68* (2006.01)
*A61K 38/16* (2006.01)

(52) U.S. Cl.
CPC ......... *G01N 33/6872* (2013.01); *A61K 38/16* (2013.01); *G01N 33/6893* (2013.01); *G01N 2333/4703* (2013.01); *G01N 2800/323* (2013.01); *G01N 2800/324* (2013.01); *G01N 2800/52* (2013.01)

(58) Field of Classification Search
CPC .......... G01N 33/6872; G01N 33/6893; G01N 2333/4703; G01N 2800/323; G01N 2800/324; G01N 2800/52; A61K 38/16
See application file for complete search history.

(56) References Cited

U.S. PATENT DOCUMENTS

2005/0153381 A1* 7/2005 Marusich ............... C07K 16/40
435/7.92

FOREIGN PATENT DOCUMENTS

WO 2006/029982 A2 3/2006

OTHER PUBLICATIONS

Genoux et al., Mitochondrial Inhibitory Factor 1 (IF1) Is Present in Human Serum and Is Positively Correlated with HDLCholesterol, PloS One, Sep. 2011, vol. 6, Issue 9, 8 pages.*
Rudolf M. Lequin, Enzyme Immunoassay (EIA)/Enzyme-Linked Immunosorbent Assay (ELISA), Clin. Chem. 51:12, 2415-2418 (2005).*
Ausubel et al., Current Protocols in Molecular Biology, 2003, John Wiley & Sons, 22 pages.*
Rouslin et al., "ATPase activity, IF-1 content, and proton conductivity of ESMP from control and ischemic slow and fast heart-rate hearts", Journal of Bioenergetics and Biomembranes, Jan. 1, 1995, pp. 459-466, vol. 27, No. 4, Plenum Publishing, New York, NY.
Di Pancrazio et al., "In vitro and in vivo studies of F(0)F(1)ATP synthase regulation by inhibitor protein IF(1) in goat heart", Biochimica et Biophysica Acta, Nov. 4, 2004, pp. 52-62, vol. 1659, No. 1.
Navab et al., "Oral D-4F Causes Formation of Pre-Beta High-Density Lipoprotein and Improves High-Density Lipoprotein-Mediated Cholesterol Efflux and Reverse Cholesterol Transport From Macrophages in Apolipoprotein E-Null Mice", Circulation, Jun. 29, 2004, pp. 3215-3220, vol. 109, No. 2, Lippincott Williams and Wilkins, US.
Chapman et al., "Cholesteryl ester transfer protein: at the heart of the action of lipid-modulating therapy with statins, fibrates, niacin, and cholesteryl ester transfer protein inhibitors", European Heart Journal, Jan. 2010, pp. 149-164, vol. 31, No. 2.
Mousa et al., "High-Density Lipoprotein Modulation Targets", Drugs of the Future, Jan. 1, 2010, pp. 33-39, vol. 35, No. 1, Prous Science.
Spillmann et al., "High-density lipoprotein-raising strategies: update 2010", Current Pharmaceutical Design, May 2010, pp. 1517-1530, vol. 16, No. 13.
Besler et al., "High-density lipoprotein-mediated anti-atherosclerotic and endothelial-protective effects: a potential novel therapeutic target in cardiovascular disease", Current Pharmaceutical Design, May 2010, pp. 1480-1493, vol. 16, No. 13.
Waksman et al., "A first-in-man, randomized, placebo-controlled study to evaluate the safety and feasibility of autologous delipidated high-density lipoprotein plasma infusions in patients with acute coronary syndrome", Journal of the American College of Cardiology, Jun. 15, 2010, pp. 2727-2735, vol. 55, No. 24.
Nissen et al., "Effect of Recombinant APOA-I Milano on Coronary Atherosclerosis in Patients WIT Acute Coronary Syndromes a Randomized Controlled Trial", JAMA the Journal of the American Medical Association, Nov. 5, 2003, pp. 2292-2300, vol. 290, No. 17, American Medical Association, US.
Genoux et al., PloS One, 2011, vol. 6, No. 9, e33949, p. 1-8.

* cited by examiner

*Primary Examiner* — Karlheinz R. Skowronek
*Assistant Examiner* — Joseph Fischer
(74) *Attorney, Agent, or Firm* — Whitham, Curtis & Cook, P.C.

(57) ABSTRACT

The present invention relates to a method for assessing a subject's risk of having a cardiovascular disease comprising the step of measuring the level of IF1 in a body fluid sample obtained from said subject wherein the level of EF1 is negatively correlated with the risk of said subject of having cardiovascular disease.

5 Claims, 3 Drawing Sheets

Figure 1:
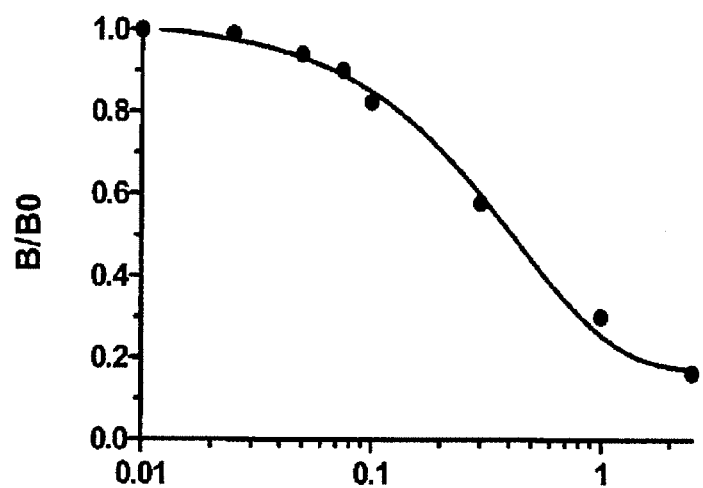

METHOD FOR MEASURING THE LEVEL OF CIRCULATING INHIBITORY FACTOR 1 PROTEIN IN A SUBJECT MEASURING THE LEVEL OF CIRCULATING INHIBITORY FACTOR 1 (IF1) PROTEIN IN A SUBJECT

CROSS-REFERENCE TO RELATED APPLICATIONS

This application is a continuation of U.S. Ser. No. 13/981, 666 filed Jul. 25, 2013, now U.S. Pat. No. 9,052,326, which was a national stage application filing of international application of PCT/EP2012/051080 filed Jan. 25, 2012, which claimed priority to U.S. Provisional Application 61/436,239 filed Jan. 26, 2011 and European Application 11305080.1 filed Jan. 26, 2011.

FIELD OF THE INVENTION

The present invention relates to a method for assessing a subject's risk of having a cardiovascular disease.

BACKGROUND OF THE INVENTION

Despite considerable advances in the treatment of cardiovascular disease (CVD), it remains one of the leading causes of death in developed countries. Several large-scale prospective epidemiological studies provided overwhelming evidence that low plasma levels of high-density lipoprotein cholesterol (HDL-C) is a major, independent risk factor for CVD. Studies in genetically modified animal models and in subjects with rare disorder of HDL metabolism support a causal relationship between low HDL and development of atherosclerotic vascular disease. It is noteworthy that a low level of HDL-C (generally regarded by current treatment guidelines as <40 mg/dL or <1.0 mmol/L in men and <50 mg/dL or <1.3 mmol/L in women) remains predictive of future cardiovascular risk, even when the concentration of cholesterol in LDL has reached low levels by treatment with statins (Barter P, Gotta A M, LaRosa J C, et al. HDL cholesterol, very low levels of LDL cholesterol, and cardiovascular events. N Engl J Med. Sep. 27, 2007; 357(13): 1301-1310).

While this atheroprotective activity of HDL is now widely accepted, the mechanism that supports this effect is still debated. The most well-established mechanism by which HDLs protect against atherosclerosis is by promoting cholesterol efflux from macrophages and transporting the cholesterol to the liver for excretion in bile and faeces, a process called 'reverse' cholesterol transport' (RCT). In addition, this ateroprotective role of HDLs may also be related to their anti-oxidative, anti-inflammatory, anti-apoptotic, or endothelial protective properties, so called pleiotropic effects (Calabresi L, Gomaraschi M, Franceschini G. Endothelial protection by high-density lipoproteins: from bench to bedside. Arterioscler Thromb Vasc Biol. Oct. 1, 2003; 23(10):1724-1731; von Eckardstein A, Hersberger M, Rohrer L. Current understanding of the metabolism and biological actions of HDL. Curr Opin Clin Nutr Metab Care. March 2005; 8(2):147-152). These protective pleiotropic effects of HDL lead to the concept that therapies to enhance plasma HDL-C levels would be anti-atherogenic and protective against cardiovascular events. However, HDLs are highly heterogeneous with subclasses that differ in density, size, charge and protein composition, which have different functions and may differ in their functional anti-atherogenic properties. Furthermore, several environmental factors, like cigarette smoking, alcohol consumption and physical activity or inflammatory condition are known to influence plasma HDL-C levels. Given the complexity of the HDL system, it has emerged that single measurement of HDL-C levels often fails to provide a reliable prediction of HDL's biological activities in protecting against CVD and thus is frequently a poor indicator of protection or risk at the individual subject level. Therefore, new biological markers reflecting vascular or metabolic activities of HDL particles are needed to better evaluate subject status regarding cardiovascular risk or to evaluate the responsiveness of subjects to the emergent HDL-related therapies.

SUMMARY OF THE INVENTION

The present invention relates to a method for assessing a subject's risk of having a cardiovascular disease comprising the step of measuring the level of inhibitor factor 1 (IF1) in a body fluid sample obtained from said subject wherein the level of IF1 is negatively correlated with the risk of said subject of having a cardiovascular disease.

A high level of IF1 is predictive of a low risk of having a cardiovascular disease.

A low level of IF1 is predictive of a high risk of having a cardiovascular disease.

The present invention also relates to a method for measuring the level of IF1 in a subject comprising the step of measuring the level of IF1 in a blood sample or a cerebrospinal fluid sample obtained from said subject.

The present invention provides a kit comprising means measuring the level of IF1 in a body fluid sample.

The invention also relates to an agent raising the level of HDL selected from the group consisting of lipid-poor apoA-I, apoA-I associated with phospholipids mixture, apoA-I mimetics and CETP inhibitors for use in the treatment of a cardiovascular disease in a subject having a low level of IF1 in blood.

DETAILED DESCRIPTION OF THE INVENTION

Definitions

Cardiovascular disease (CVD) is the general term for heart and blood vessel diseases, including atherosclerosis, coronary heart disease, cerebrovascular disease, aorto-iliac disease, and peripheral vascular disease. Subjects with CVD may develop a number of complications, including, but not limited to, myocardial infarction, stroke, angina pectoris, transient ischemic attacks, congestive heart failure, aortic aneurysm and death.

As used herein, the term "subject" denotes a mammal, such as a rodent, a feline, a canine, and a primate. Preferably, a subject according to the invention is a human.

The term "IF1" should be understood broadly, it encompasses the mature IF1, isoforms thereof and fragments thereof.

IF1 (inhibitor factor 1) regulates the ATPase activity of mitochondrial $F_1F_O$-ATP synthase (Pullman M E et al. (1963)). IF1 is a basic mitochondrial protein of 10 kDa encoded by a nuclear gene with a significant degree of homology in various species (Green D W et al. (2000)). IF1 binds through its N-terminal region at the interface between $\alpha$ and $\beta$ subunits of the $F_1$ catalytic sector of mitochondrial ATP synthase, thereby blocking rotary catalysis (Cabezon E et al., (2003)). It has been reported that exogenous IF1 could specifically bind to cell surface ATP synthase (also called ecto-F1-ATPase) on hepatocytes and endothelial cells and reduce its hydrolytic activity (Martinez L O et al. (2003); Mangiullo R et al., (2008); (Burwick N R et al., (2005)). Examples of documents disclosing IF1 are Lebowitz et al. (1993); Jackson et al., (1988); Martinez et al. (2003); Mimura et al., (1993); Solaini et al., (1997) and WO98/33909.

Recent reports have described the presence of IF1 at the plasma membrane of different cells types such as hepatocytes and endothelial cells (Burwick N R et al., (2005); Cortes-Hernandez P et al. (2005); Contessi S et al. (2007); Giorgio V et al. (2010)).

Alternative splicing occurs at IF1 locus and three transcript variants encoding distinct IF1 isoforms have been identified in humans (provided by Ref Seq http://www.ncbi.nlm.nih.gov/RefSeq/). All precursor isoforms contain an identical mitochondrial signal peptide (or transit peptide) of 25 amino acids. Mature and functional IF1 isoforms do not contain this transit peptide. IF1 variant 1 encodes the longest isoform, IF1 isoform 1, consisting of a 106 amino acid precursor protein and a 81 amino acid mature protein (ATIF1_HUMAN; REFSEQ: accession NM_016311.3, Accession number Swiss-Prot: Q9UII2 (Ichikawa N et al.; (1999)).

IF1 variant 2 encodes IF1 isoform 2 consisting of a 71 amino acid precursor protein and a 46 amino acid mature protein (A6NE74_HUMAN; REFSEQ: accession NM_178190.1). Isoform 2 has a shorter and distinct C-terminus compared to isoform 1, because of an alternate splice site in the 3' coding region and a frameshift.

IF1 variant 3 encodes the shorter isoform, IF1 isoform 3, consisting of a 60 amino acid precursor protein and a 35 amino acid mature protein (REFSEQ: accession NM_178191.1). Variant 3 is identical to variant 1 but without the last 46 C-terminus amino acids.

In a preferred embodiment, IF1 is IF1 isoform 1.
In another embodiment, IF1 is IF1 isoform 2.
In another embodiment, IF1 is IF1 isoform 3.

Assay Method

The present invention relates to a method for measuring the level of IF1 in a subject comprising the step of measuring the level of IF1 in a blood sample or a cerebrospinal fluid sample obtained from said subject.

Indeed, the inventors have surprisingly demonstrated that IF1, known until now to be present in mitochondria or at the plasma membrane, is a circulating protein present in blood.

In one embodiment, the blood sample to be used in the methods according to the invention is a whole blood sample, a serum sample, or a plasma sample. In a preferred embodiment, the blood sample is a serum sample.

In another embodiment, the level of IF1 is measured in a cerebrospinal fluid sample.

Indeed, ATP synthase inhibited by IF1 is present on plasma membrane of some cerebral cells.

Particularly, ATP synthase has been found at the cell surface of culture hippocampal neurons and astrocytes (Schmidt C et al., (2008)).

Once the body fluid sample from the subject is prepared, the level of IF1 may be measured by any known method in the art.

For example, the concentration of IF1 may be measured by using standard electrophoretic and immunodiagnostic techniques, including immunoassays such as competition, direct reaction, or sandwich type assays. Such assays include, but are not limited to, Western blots, agglutination tests, enzyme-labeled and mediated immunoassays such as ELISA, biotin/avidin type assays, radioimmunoassays, immunoelectrophoresis, immunoprecipitation, high performance liquid chromatography (HPLC), size exclusion chromatography, solid-phase affinity, etc.

In a particular embodiment, such methods comprise contacting the body fluid sample with a binding partner.

As used therein, binding partner refers to a molecule capable of selectively interacting with IF1.

The binding partner may be generally an antibody that may be polyclonal or monoclonal preferably monoclonal. Polyclonal antibodies directed against IF1 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against IF1 can be prepared and isolated using any technique that provides for the production of antibody molecules by continuous cell lines in culture. Techniques for production and isolation include but are not limited to the hybridoma technique originally described by Kohler et al. Nature. 1975; 256(5517):495-7; the human B-cell hybridoma technique (Cote et al Proc Natl Acad Sci USA. 1983; 80(7):2026-30); and the EBV-hybridoma technique (Cole et al., 1985, in "Monoclonal Antibodies and Cancer Therapy," Alan R. Liss, Inc. pp. 77-96). Alternatively, techniques described for the production of single chain antibodies (see e.g. U.S. Pat. No. 4,946,778) can be adapted to produce anti-IF1, single chain antibodies. Antibodies useful in practicing the present invention also include anti-IF1 including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to IF1. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk et al. (1990) Science, 249, 505-510. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena 1999. Peptide aptamers consist of conformationally constrained antibody variable regions displayed by a platform protein, such as *E. coli* Thioredoxin A, that are selected from combinatorial libraries by two hybrid methods (Colas et al. (1996) Nature, 380, 548-50).

The binding partners of the invention such as antibodies or aptamers, may be labeled with a detectable molecule or substance, such as a fluorescent molecule, a radioactive molecule or any others labels known in the art. Labels are known in the art that generally provide (either directly or indirectly) a signal.

As used herein, the term "labeled", with regard to the binding partner, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labeling of the probe or antibody by reactivity with a detectable substance. An antibody or aptamer of the invention may be labeled with a radioactive molecule by any method known in the art. For example radioactive molecules include but are not limited radioactive atom for scintigraphic studies such as I123, I124, In111, Re186, Re188.

The aforementioned assays generally involve the bounding of the binding partner (ie. antibody or aptamer) in a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like. More particularly, an ELISA method can be used, wherein the wells of a microtiter plate are coated with a set of antibodies against IF1. A body fluid sample containing or suspected of containing IF1 is then added to the coated wells. After a period of incubation sufficient to allow the formation of binding partner-IF1 complexes, the plate(s) can be washed to remove unbound material and a labeled secondary binding molecule added. The secondary binding molecule is allowed to react with any captured sample marker protein, the plate washed and the presence of the secondary binding molecule detected using methods well known in the art.

As the binding partner, the secondary binding molecule may be labeled.

Different immunoassays, such as radioimmunoassay or ELISA, have been described in the art.

Measuring the concentration of IF1 with or without immunoassay-based methods may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, IF1 may be identified based on the known "separation profile" e. g., retention time, for that protein and measured using standard techniques. Alternatively, the separated proteins may be detected and measured by, for example, a mass spectrometer.

The concentration of IF1 may also be determined by measuring the activity of $F_1$-ATPase using an ATP-regenerating system as previously described (van Raaij M J et al., (1996)). One unit of IF1 is defined as the amount that inhibits 0.2 U of ATPase by 50%, where 1 U of ATPase hydrolyzes 1 μmol of ATP/min. Activity of IF1 can be essayed for the inhibition of ATPase of either bovine submitochondrial particles that had been depleted of endogenous IF1, or of isolated, nucleotide-stripped and inhibitor-free, F1-ATPase (van Raaij M J et al., (1996)).

In a preferred embodiment, the method for measuring the level of IF1 comprises the step of contacting the blood sample or the cerebrospinal fluid sample with a binding partner capable of selectively interacting with IF1 to allow formation of a binding partner-IF1 complex.

In more preferred embodiment, the method according to the invention comprises further the steps of separating any unbound material of the blood sample or the cerebrospinal fluid sample from the binding partner-IF1 complex, contacting the binding partner-IF1 complex with a labelled secondary binding molecule, separating any unbound secondary binding molecule from secondary binding molecule-IF1 complexes and measuring the level of the secondary binding molecule of the secondary binding molecule-IF1 complexes.

The invention also provides a kit comprising means for measuring the level of IF1 in a body fluid sample.

The kit according to the invention may comprise a solid support, a binding partner capable of selectively interacting with IF1 that is bound to said solid support and an assay for measuring the level of the binding partner-IF1 complex.

In a preferred embodiment, the binding partner of the invention is an antibody binding to circulating IF1.

As used herein, circulating IF1 refers to IF1 that is found in a body fluid of a subject, in particular within the blood circulation.

Certain antibodies against IF1 do not bind circulating IF1. For example, the anti-IF1 commercially available from Invitrogen under clone ID 5ED7, does not bind to circulating IF1.

In order to assay if an anti-IF1 antibody binds to circulating IF1, anti-IF1 antibody may be tested by a immunoprecipitation, as described, for example in Plosone, September 2011, by Genoux A. et al.

For example, immunoprecipitation of circulating IF1 may be performed using Pierce H Crosslink Immunoprecipitation Kit (ThermoScientific) according to manufacturer's instructions. 10 mg of anti-IF1 antibody to test are covalently crosslinked onto protein AG resin and then incubated overnight with 2 mg of 500 mg of proteins from low-abundance protein-enriched serum. 2 mg of recombinant IF1 (rIF1) or 500 mg of proteins from HepG2 cell after cell lysis may be used as positive control.

After washing, the bound proteins are eluted in 0.2 M glycine pH 2.8 and 56 Laemmli sample buffer is added. The presence of IF1 is controlled in the eluted fractions.

In a preferred embodiment, the kit is for an ELISA.
Diagnostic Method:

The invention also provides a method for assessing a subject's risk of having a cardiovascular disease comprising the step of measuring the level of IF1 in a body fluid sample obtained from said subject wherein the level of IF1 is negatively correlated with the risk of said subject of having a cardiovascular disease.

Indeed, besides having discovered that IF1 is circulating, the inventors have also demonstrated that the level of circulating IF1 is negatively correlated with CVD risk.

A high level of IF1 is predictive of a low risk of having a cardiovascular disease.

A low level of IF1 is predictive of a high risk of having a cardiovascular disease.

In a preferred embodiment, the body fluid sample is a blood sample (e.g. a whole blood sample, a serum sample, or a plasma sample).

Typically, a high or a low level of IF1 is intended by comparison to a median control value or by comparison respectively to an upper or a lower control value.

Said control values may be determined in regard to the level of IF1 present in samples taken from one or more healthy subject or to the WE distribution in a control population.

In one embodiment, the method according to the present invention comprises the step of comparing said level of IF1 to an upper and/or a lower control value wherein a high level of IF1 compared to said upper control value is predictive of a low risk of having a cardiovascular disease and a low level of IF1 compared to said lower control value is predictive of a high risk of having a cardiovascular disease.

The control values may depend on various parameters such as the method used to measure the level of IF1 or the gender of the subject.

Typically, for a level of IF1 in a serum sample measured using a competitive immunoassay with a polyclonal antibody raised against human IF1, a level of IF1 superior to 0.65 μg/ml, to 0.7 μg/ml, to 0.75 μg/ml, to 0.8 μg/ml or to 0.85 μg/ml is predictive of a low risk of having a cardiovascular disease and a level of IF1 lower than 0.45 μg/ml, than 0.4 μg/ml, than 0.35 μg/ml, than 0.3 μg/ml, than 0.25 μg/ml is predictive of a high risk of having a cardiovascular disease.

This correlation between the level of IF1 and the risk of having a CVD is independent from environmental markers of CVD risk as physical activity, cigarette smoking etc. . . .

Therefore, IF1 is a new and efficient marker of CVD risk.

In one embodiment, the subject is not otherwise known to be at an elevated risk of having a cardiovascular disease.

The method according to the invention may also be combined with other methods for assessing the risk to have a cardiovascular disease. Examples of such methods are well-known in the art.

Classical methods for evaluating risk factors include, but are not limited to, assessments of personal and/or familial history of CVD, tobacco consumption, measurements of blood pressure, plasma glucose, low-density lipoprotein (LDL) and high-density lipoprotein (HDL) cholesterol, cholesterol, triglycerides and the like.

In particular, IF1 levels will provide additive predictive value in those patients with low levels of HDL-cholesterol and/or apolipoprotein A-I.

The present invention also relates to a method for assessing the seriousness of a cardiovascular disease in a subject having said cardiovascular disease comprising the step of measuring the level of IF1 in a body fluid sample obtained from said subject wherein the level of IF1 is negatively correlated with the seriousness of the cardiovascular disease in said subject.

Indeed, the inventors have found that in bivariate analyses, the average Gensini score, reflecting the seriousness of coronary artery disease, regularly decreased as plasma IF1 concentrations are more elevated.

The Gensini score is one of the most used assays to estimate the seriousness of coronary artery disease (CAD), as defined above. It combines the number of observed stenoses, each one being attributed a score number according to the importance of the narrowing and a coefficient reflecting the localization of the lesion in the coronary tree (Gensini G G. (1983)). These results were confirmed by using angiography, another method for assessing the seriousness of a cardiovascular disease. Angiography objectifies the seriousness of coronary artery lesions. Angiograms are interpreted by two independent operators. Different scores can be calculated which take into account the number of stenoses, the degree of intra-luminal narrowing and the geographical importance of the stenosis in the coronary tree.

The method for assessing the seriousness of a cardiovascular disease according to the invention could be combined with other well known methods, such as the Gensini score or for each coronary stenosis, the degree of luminal narrowing and its geographic importance.

The present invention also relates to method for monitoring the effect of a therapy for treating cardiovascular disease in a subject comprising the step of measuring the level of IF1 in a first body fluid sample obtained from said subject at t1 and measuring the level of IF1 in a second body fluid sample obtained from said subject at t2 wherein when t1 is prior to therapy, t2 is during or following therapy, and when t1 is during therapy, t2 is later during therapy or following therapy, and wherein an increase in the level of IF1 in the second sample as compared to the level of IF1 in the first sample is indicative of a positive effect of the therapy on cardiovascular disease in the treated subject.

Further to current statin therapies against cardiovascular disease, HDL therapies are developed. These therapies aim at raising the level of HDL. Indeed, as described above, there is an inverse correlation between HDL and CVD risk. Thus, it has been disclosed that raising HDL 1 mg/dl reduces the risk of CVD by 2 or 3% (Gordon D J, Rifkind B M. High-density lipoprotein: the clinical implications of recent studies. N Engl J Med. 1989; 321: 1311-1316; Castelli W P, Anderson K, Wilson P W, Levy D. Lipids and risk of coronary heart disease: The Framingham Study. Ann Epidemiol. 1992; 2: 23-28).

There are several therapeutics approaches in HDL therapy. Main approaches are to raise the level of HDL or apolipoprotein A-I (apoA-I), the main atheroprotective apolipoprotein of HDL. Parental infusion of full-length lipid-poor apoA-I or apoA-I associated with phospholipids mixture might be expected to have beneficial effects that, with repeated infusions, could favourably impact on atherosclerosis (Nissen S E et al., (2003)). Selective delipidation of HDL ex-vivo, which generates lipid-poor apoA-I is an alternative strategy; in this model the delipidated HDL is reinfused in patient and might decrease the development of atherosclerosis (Waksman R et al., (2010)). ApoA-I mimetics are other therapeutics approaches in HDL therapy. These apoA-I mimetics are small amphipathic peptide of 18-22 amino acids based loosely on the apoA-I sequence have similar properties to apoA-I, including the abilities to promotes excess cholesterol removal from tissues (Navab M et al., (2005)). One major advantage of these apoA-I mimetic peptides over full-length apoA-I is that they are cheaper and easier to make as a therapeutic molecule.

Several ApoA-I mimetics have been identified; these included ETC-216 BY Esperion, D-4F by Kos Pharmaceuticals, AVP-26452 by Astrazeneca. Examples of such drugs are disclosed in Navab M et al. (2005); Garber D W et al. (2001); Navab M et al. (2004); Navab M et al. (2006) and WO2010093918.

Most known drugs which inhibit HDL degradation are CETP inhibitors. The term "CTP inhibitors" refers to compounds that inhibit the cholesteryl ester transfer protein (CETP)-mediated transport of various cholesteryl esters and triglycerides from HDL to LDL and VLDL.

CETP inhibitors are well known to those skilled in the art. Examples of patents disclosing CETP inhibitors are WO2009071509, WO2009059943, WO2008082567, EP2007726, EP1973889, U.S. Pat. No. 6,140,343, U.S. Pat.

Nos. 6,197,786, 6,723,752, WO2006/014357; WO2006/014413, WO2007/079186, EP1670765 or U.S. Pat. No. 5,512,548.

Several efficacious chemical CETP inhibitors have been identified; these include torcetrapib (Pfizer, New York, N.Y., USA), dalcetrapib (previously referred to as RO4607381/JTT-705, Roche/Japan Tobacco, Basel, Switzerland), and anacetrapib (MK-0859, Merck & Co., Whitehouse Station, N.J., USA). Molecular insight into the mechanism of action of these inhibitors has become possible as a result of the definition of the crystal structure of CETP (see for example Chapman et al., European Heart Journal (2010) 31, 149-164 for review).

The invention also relates to a method for treating a cardiovascular disease in a subject having a low level of IF1 in blood with an agent raising the level of HDL selected from the group consisting of lipid-poor apoA-I, apoA-I associated with phospholipids mixture, apoA-I mimetics and CETP inhibitors.

The invention also relates to an agent raising the level of HDL selected from the group consisting of lipid-poor apoA-I, apoA-I associated with phospholipids mixture, apoA-I mimetics and CETP inhibitors for use in the treatment of a cardiovascular disease in a subject having a low level of IF1 in blood.

Typically, a body fluid sample is obtained from the subject and the level of IF1 is measured in this sample, together with evaluation of plasma lipids, HDL and LDL-cholesterol and/or apolipoproteins A-I and B. Indeed, statistical analyses revealed that raising IF-1 levels would be particularly beneficial in those patients displaying low levels of HDL-cholesterol and/or apolipoprotein A-I.

In a preferred embodiment, the cardiovascular disease is a coronary artery disease.

In a preferred embodiment, the cardiovascular disease is atherosclerosis.

The invention also relates to the use of IF1 as a marker of cardiovascular risk.

The invention will be further illustrated by the following figures and examples. However, these examples and figures should not be interpreted in any way as limiting the scope of the present invention.

FIGURE LEGENDS

FIG. 1: Typical standard curve used for IF1 quantification.

Figure 2:
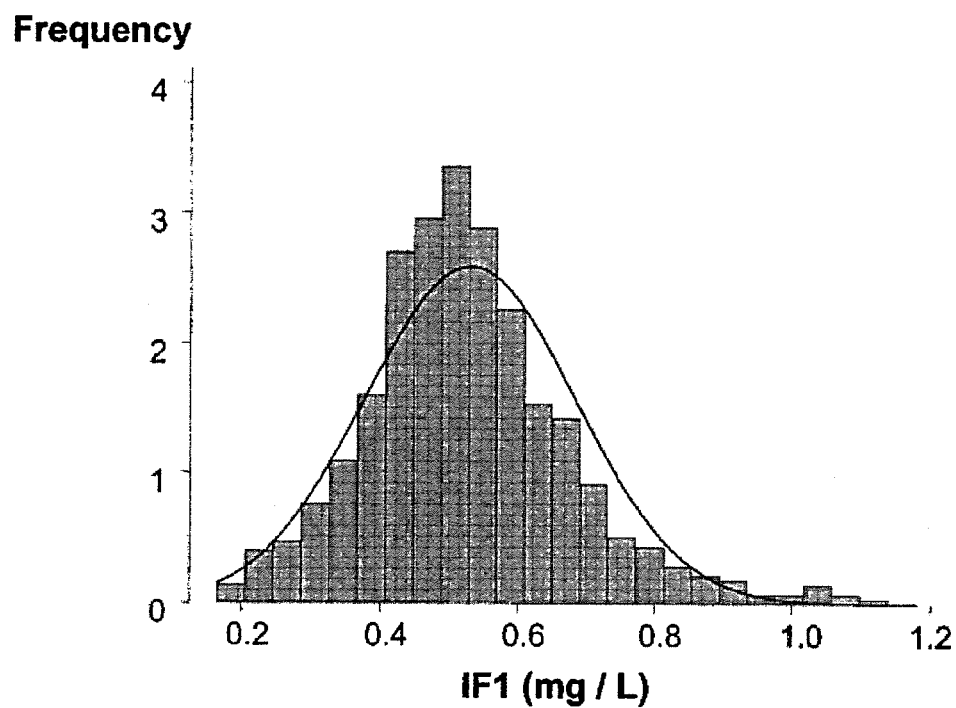

FIG. 2: IF1 frequency distribution in the general population. Density histogram with normal density plot of IF1. IF1 was measured in 669 controls aged 45-74.

Figure 3:
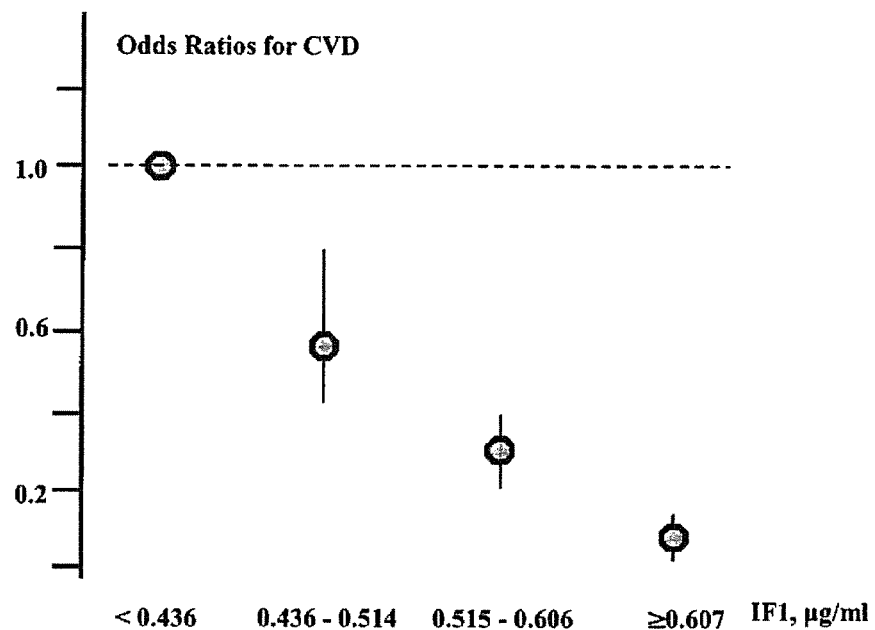

FIG. 3: Relative risk of CVD as a function of IF1.

Figure 4:
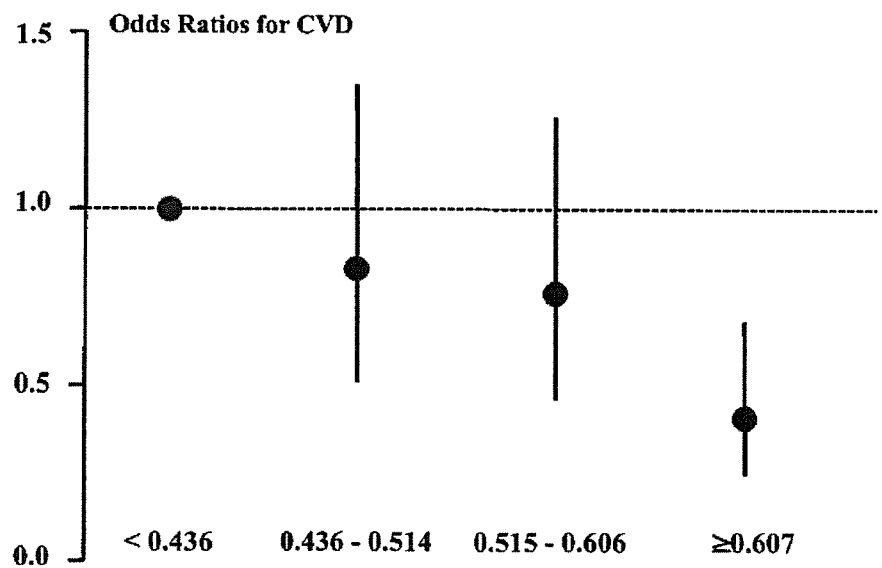

FIG. 4: Relative risk of CVD as a function of IF1 after adjustment for education, physical activity, smoking and alcohol habits, diabetes, dyslipidemia, hypertension, C reactive protein (CRP) and apoA-I levels.

Figure 5:
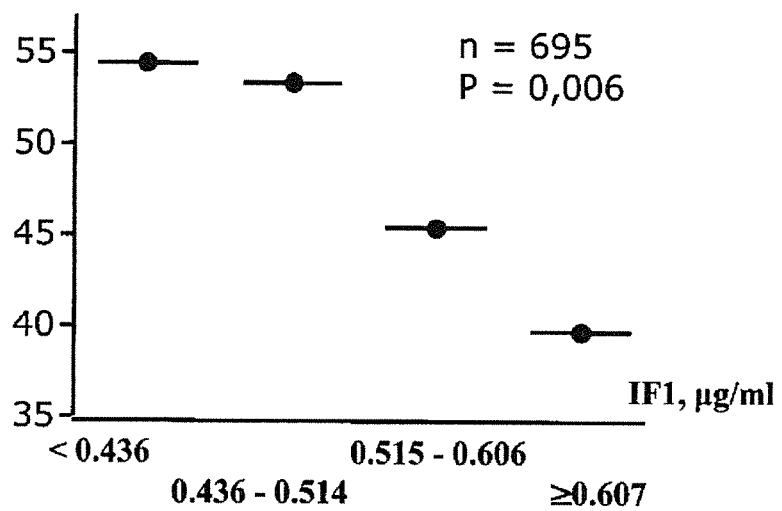

FIG. 5: Seriousness of coronary injuries as a function of IF1—Gensini score

Figure 6:
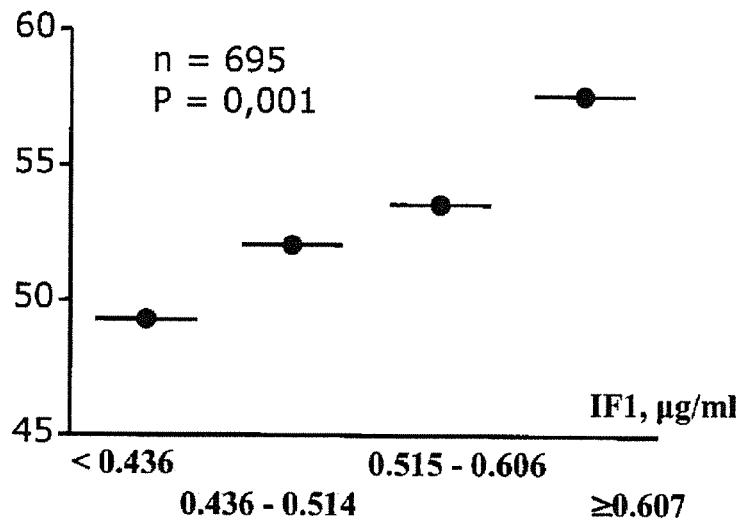

FIG. 6: Seriousness of coronary injuries as a function of IF1—Left ventricular ejection fraction (%)

EXAMPLE

Materials and Methods
Sample Treatment for Mass Spectrometry Analysis

100 µl of serum from 10 individuals selected within the general population of GENES cohort were pooled together. The GENES study is a research on genetic and environmental determinants of coronary artery disease conducted in the frame of a large cross-sectional case-control at Toulouse University Hospital.

This plasma pool was then pre-fractioned using the ProteoMiner™ kit (Bio-Rad Laboratories) according to the manufacturer's protocol. The protein concentration of sample was 2.5 g/L. The equalized plasma sample was stored at −80° C. until mass spectrometry analysis.

The total volume of ProteoMiner™ elution from plasma sample was diluted in Laemmli sample buffer. Reduction and alkylation of cysteines were performed by 1 hour incubation at room temperature (20 mM DTT are contained in Laemmli sample buffer) followed by addition of 90 mM iodoacetamide for 30 min at room temperature in the dark. The sample has then been loaded on four lanes of a 15% acrylamide SDS-PAGE gel and four other lanes were loaded on the same gel with 5 µg of recombinant human IF1, rIF1. The proteins were visualized by Coomassie Blue staining and four visible bands corresponding to rIF1 were cut. In parallel, a slice was cut at the same molecular weight size than rIF1 in each of the four plasma sample lane. The gel slices were washed with three cycles of 100 mM ammonium bicarbonate wash for 15 min at 37° C. followed by a second wash in 100 mM ammonium bicarbonate, acetonitrile (1:1) for 15 min at 37° C. Proteins were digested by incubating each gel slice with 0.6 µg of modified sequencing grade trypsin (Promega) in 50 mM ammonium bicarbonate overnight at 37° C. The resulting peptides were extracted from the gel by three steps which were pooled together: a first incubation in 50 mM ammonium bicarbonate for 15 min at 37° C. and two incubations in 10% formic acid, acetonitrile (1:1) for 15 min at 37° C., and pooled together. The four peptide extractions corresponding to the same initial sample (rIF1 or plasma sample) were combined and the dried in a SpeedVac, and resuspended in 5% acetonitrile, 0.05% trifluoroacetic acid.

Targeted Analysis by Multiple Reaction Monitoring

The peptides mixture from rIF1 was used for optimisation of human IF1 detection by nanoLC/MS in Multiple Reaction Monitoring (MRM) mode using an Ultimate3000 system (Dionex, Amsterdam, The Netherlands) coupled to an 5500 QTrap mass spectrometer (AB Sciex, Foster City, Calif., USA). 1 pmol of rIF1 was loaded on a C18 precolumn (300-µm inner diameter×5 mm, Dionex, Amsterdam, The Netherlands) at 20 µl/min in 2% acetonitrile, 0.05% trifluoroacetic acid. After 3-min desalting, the precolumn was switched on line with the analytical column (75-µm inner diameter×15 cm silica capillary tubing packed with Reprosil-Pur C18-AQ 3 µm phase, Dr. Maisch, GmbH, Germany) equilibrated in 100% solvent A (5% acetonitrile, 0.2% formic acid). Peptides were eluted using a 0-50% gradient of solvent B (80% acetonitrile, 0.2% formic acid) during 25 min at 300 nl/min flow rate. The 5500 QTrap was operated in MRM mode with the Analyst software (version 1.5.1, AB Sciex, Foster City, Calif., USA). The four peptides of human IF1 giving the most intense signals were monitored in MRM with quadrupole Q1 and Q3 set to Unit resolution, optimal collision energies and declustering potentials were determinated for three parent/fragment transitions of each peptide. During the run, full scan MSMS acquisitions (EPI, Enhanced Product Ion) were also triggered when MRM signal exceeded 200 counts, with a mass tolerance of 250 mDa, the Linear Ion Trap (LIT) was set at 150 ms fixed fill time. A third of the peptides extract from plasma sample was then loaded on the system in the same way than rIF1 and the analysis by the 5500QTrap was performed in the same mode (MRM+EPI) with the optimized transition list. A blank run in the same conditions was performed before analyzing the plasma sample in order to ensure the non-contamination of the nanoLC system by rIF1.

Database Search

The Mascot Daemon software (version 2.3.2, Matrix Science, London, UK) was used to perform database searches. To automatically extract peak lists from Analyst wiff files, the Mascot.dll macro (version 1.6b27) provided with Analyst was used and set for no grouping of MS/MS scans. Data were searched against *Homo sapiens* entries in the Uniprot protein database (September 2010 version—96635 sequences). Carbamidomethylation of cysteines was set as a fixed modification and oxidation of methionines and deamidation of asparagines and glutamines were set as variable modifications for Mascot searches. Specificity of trypsin digestion was set for cleavage after Lys or Arg except before Pro, and two missed trypsin cleavage sites were allowed. The mass tolerances in MS and MSMS were set to 0.6 Da, and the instrument setting was specified as "ESI-QUAD".

Construction of Bacterial Expression Plasmid.

The sequence encoding the mature peptide of human IF1, without the sequence of the mitochondrial targeting signal (MTS), was amplified by PCR from HeLa cell cDNA. The amplified fragment was then introduced at BamHI/HindIII restriction sites into VariFlex Expression vector pBEn-SBP-SET1-Qa (Stratagene) containing the Streptavidin Binding Peptide coding sequence (SBP tag) and a thrombin protease cleavage site to allow fusion of the SPB tag at the N-terminus of the cloned protein-coding sequence. The resulting expression plasmid, containing the entire mature human IF1, is verified by DNA sequencing and known as pBEn-SBP-IF1.

Overexpression of Human IF1 in *Escherichia coli*.

A colony of recently transformed cells of *E. coli* BL21 (DE3) was inoculated into 30 mL of Terrific broth medium (Ozyme) containing 100 µg/mL ampicillin. The culture was grown overnight with shaking in a 1 L flask at 37° C. Expression of the protein was induced by addition of 150 mL of Terrific broth medium containing 100 mM IPTG, and growth was continued for a further 3-4 h. The bacteria were centrifuged (7000 g, 15 min, 4° C.) and the bacterial pellet was kept at −20° C.

Purification of Bacterially Expressed Human IF1.

All the procedures were carried out at 4° C. The bacterial pellet containing the recombinant IF1 protein was resuspended in 20 mL lysis buffer (0.5M NaCl, 0.7M saccharose, 1 mM EDTA, 1% Triton X-100, 5 mM β-mercaptoethanol, 1× Roche protease inhibitor Cocktail) then sonicated 3 times for 100 s. The recombinant proteins were soluble in the cytoplasmic fraction which was clarified by high speed centrifugation (130 000 g, 1 h, 4° C.). The broken cell supernatant containing IF1 was diluted in binding buffer (50 mM ammonium carbonate, 0.5 M NaCl, pH 10.0) to a final concentration of 1 mg/mL and filtered through a 0.22 µm filter then was applied at 1 mL/min to a HiTrap™ Streptavidin HP 1 mL column (GE Healthcare) equilibrated in binding buffer. The column was washed until the optical density at 280 nm had reached 0.1 then IF1 was eluted from the column in 6M guanidine elution buffer. Pooled fractions containing IF1 protein fused with SBP tag were dialyzed 3 times against thrombin cleavage buffer (20 mM Tris-HCl pH8.4, 150 mM NaCl, 2.5 mM CaCl2) and thrombin (IOU mg protein) was added overnight at RT in order to clive the SPB tag. The sample was then loaded onto HiTrap™ Streptavidin HP 1 mL column and pure IF1 was found in the flow-through fraction. Human recombinant IF1 was >95% pure as determine by SDS-PAGE (data not shown).

IF1 Antiserum Preparation

A polyclonal antibody was raised in New Zealand White rabbits against recombinant human IF1. Total serum IgG was purified from serum by affinity chromatography with the use of protein A Sepharose CL-4B columns (GE healthcare), according to manufacturer's instruction. Purity of IgG fractions was assessed by sodium dodecyl sulfate-polyacrylamide gel electrophoresis (SOS-PAGE). Specific IgG against IF1 were purified from total serum IgG by affinity chromatography with the use of IF1 column.

Immunofluorescenee

HeLa cells cultured on coverslips were incubated with Mitotracker for 30 min at 37° C. when indicated. Then, cells were washed, fixed with 4% paraformaldehyde and permeabilized with 0.1% Triton X-100 for 60 min. After saturation of unspecific sites with PBS containing 10% FCS, cells were first incubated with the primary antibody (monoclonal anti-alpha ATP synthase from Invitrogen; polyclonal anti-IF1 antibody) then with fluorescently labeled secondary antibodies from Jackson Immunoresearch Laboratories (West Grove, Pa.). Pictures were captured using a Zeiss LSM 510 META confocal microscope equipped with a 63× Plan-Apochromat objective.

SPR (Biacore) Analysis.

Purified anti-IF1 antibody was immobilized by amine linkage on CM5 chips (Biacore AB) after NHS-EDC activation. Binding was analysed in a Biacore 3000 apparatus. Increasing concentration of recombinant human IF1 were injected at a flow rate of 20 µL/min, exposed to the surface for 175 s (association phase), followed by a 200 s flow running during which dissociation occurred. Between injections, in order to recover the prebinding baseline, the sensorchip surface was regenerated by a 5 µL injection of 0.01% SDS (15 s of contact time). The apparent Kd value, was calculated with the CLAMP software (Myszka D G, Morton T A, CLAMP: a biosensor kinetic data analysis program, Trends Biochem Sci. 1998 April; 23(4): 149-50).

Immunoassay of IF1

A competitive immunoassay was devised in order to quantify IF1 in human sera. The wells of 96-well Polysorb ELISA plates (NUNC, Roskilde, Denmark) were coated with 100 µl of recombinant human IF1 (0.5 µg/ml) diluted in bicarbonate buffer (0.1 M, pH=9.6). The plates were incubated overnight at room temperature (RT) to allow complete binding. Serum samples were defrozen at room temperature and centrifugated (2 000×g, 10 min). 50 µl of each subject serum (diluted with 50 µl of PBS IX), or 100 µl of each recombinant human IF1 standard (0; 0.025; 0.050; 0.075; 0.1; 0.3; 1 and 2.5 µg/ml), were incubated with 100 µl of biotinylated anti-IF1 polyclonal antibody (dilution: 1/1000 in PBS-Tween 0.05%-1% BSA buffer) overnight at 4° C. The plates were then washed 3-times with PBS buffer pH7.4 W/0.05% Tween20 and incubated with 200 µl per well of blocking buffer (PBS buffer pH7.4 W/3% BSA) for 1 hour at RT. After washing 3-times with PBS, the mixtures sample antibody were added to the wells and incubated for 4 hours at RT. The plates were washed again and incubated with 100 µl per well of streptavidin-HRP (dilution: 1/5000 in PBS pH7.4 W/0.05% Tween 1% BSA buffer) (Invitrogen, Cergy Pontoise, France) for 1 hour at RT. After washing 3-times with PBS W/0.05% Tween, plates were incubated with 200 µl per well of horseradish peroxidase (HRP) substrate TMB (3,3',5,5'-tetramethylbenzidine) for 20 minutes at RT. The reaction was stopped with 50 µl per well of HCl 1N, and the plates were then read at 450 nm in a microplate reader (Varioscan Flash, Thermo electron corporation). The 570 nm optic density (background) was subtracted. Sample concentrations were determined using the standard curve (fit type: four parameter logistic). FIG. 1 displays a typical standard curve, in the range of 0.025 to 2.5 µg IF1/ml. Fifty percent displacement was obtained for a concentration of 0.4 µg/ml. Repeatability (within the same day) and reproducibility (10 measurements over a 6-month period) gave variation coefficients of 6-7%. An average recovery of 96.8% was measured in dilution experiments. Resistance to freezing and thawing was assessed in different occasions with a 95%-103% agreement between measurements. With regards to possible correlations of IF1 with HDL markers, competition experiments with purified apolipoproteins A-I and A-II indicated no cross reactivity in this immunoassay.

CVD Subjects and Control Subjects

Serum IF1 was evaluated both in the general population and in cardiovascular disease (CVD) subjects. Evaluation was conducted in the frame of the GENES. A biological sample collection has been constituted (declared as DC-2008-403 #1 to the Ministry of Research and to the Regional Health Agency).

Cases were subjects admitted for a first coronary event, either unstable angina pectoris or definite myocardial infarction. All cases were assessed according to a strict protocol, including clinical, electro-cardiographic, biological and angiographic criteria. They were explored for evaluation of risk factors after ≥3-month delay following CVD event. Controls were randomly selected from the general population, using electoral rolls. Cases and control subjects were paired for age. Altogether, the cohort included 791 CVD male subjects and 817 age-paired controls, aged 45-75. Data were collected on dietary habits, physical activity, alcohol and tobacco consumptions, educational level. Presence of dyslipidemia, diabetes or hypertension was assessed either from the subject's current treatments or from the clinical and biological evaluation of the subject during the investigation. Clinical investigation included anthropometric variables, blood pressure and heart rate, and for CVD cases, a complete cardiological evaluation. Biological measurements were focused on lipids and lipoproteins, glucose and insulin, gamma GT and sensitive CRP. Serum IF1 was measured in the first 669 controls and 648 cases.

Results

Characterization of IF1 in Human Plasma

The presence of IF1 in human serum was demonstrated unambiguously by mass spectroscopy analysis.

Characterization of Anti-IF1 Antibody

The interaction of recombinant human IF1 (rIF1) with polyclonal anti-IF1 antibody was controlled by surface Plasmon resonance (SPR) analysis. In these conditions, rIF1 specifically bound anti-IF1 immobilized onto SPR chips (KD=6.1 nM). To further evaluate the specificity of anti-IF1 antibody, immunofluorescence experiments were performed in HeLa cells. Immunolabeling using the anti-IF1 antibody showed a characteristic mitochondrial pattern. This is further confirmed by colocalization of IF1 staining with mitochondrial markers such as MitoTracker or the alpha subunit of ATP synthase. These data indicate that the anti-IF1 antibody was able to recognize specifically endogenous mitochondrial IF1.

Serum IF1 Levels in the General Population

Plotting of IF1 levels in the general male population evidenced a normal distribution, with a median value at 0.53 µg/ml and a 95% confidence interval of 0.24-0.82 µg/ml. (FIG. 2)

Correlation with Plasma Lipids Parameters

Correlations between IF1 levels and plasma lipids levels parameters were investigated. Plasma IF1 was positively correlated with HDL-cholesterol, apo A-I and lipoparticle AI levels, and negatively with triglycerides, apolipoprotein B and apo B-containing lipoproteins. IF1, HDL-C and apo A-I were all negatively correlated with body mass index and waist circumference. Several environmental factors, like cigarette smoking, alcohol consumption and physical activity or an inflammatory condition as documented by elevated CRP, displayed expected correlations with HDL-C or apo A-I. By contrast, correlations of those factors with IF1 were poor or absent (Table I). This indicates that correlations between IF1 and HDL markers are independent of environmental variables.

TABLE 1

Correlation between IFI, apoA-I and HDL-cholesterol and other risk factors in the general population

| Parameters | Spearman rank correlation with IF1 (mg/L), p | Spearman rank correlation with apoA-I (g/L), p | Spearman rank correlation with HDL-cholesterol (g/L), p |
|---|---|---|---|
| HDL-cholesterol (g/L) | 0.24, *** | 0.82, *** | 1 |
| ApoA-I (g/L) | 0.27, *** | 1 | 0.82, *** |
| ApoB (g/L) | −0.17, *** | −0.07, NS | −0.15, *** |
| Triglycerides (g/L) | −0.25, *** | −0.19, *** | −0.48, *** |
| LpB:CIII (mg/L) | −0.14, *** | −0.06, NS | −0.34, *** |
| Lp B:E (mg/L) | −0.26, *** | −0.21, *** | −0.25, *** |
| Body mass index (BMI) | −0.17, *** | −0.20, *** | −0.33, *** |
| Systolic blood pressure (mmHg) | −0.02, NS | 0.01, NS | −0.08, * |
| Physical activity score | 0.01, NS | 0.09, * | 0.20, *** |
| Alcohol (g/day) | 0.09, * | 0.28, *** | 0.20, *** |
| Cigaret (/day) | −0.03, NS | −0.10, * | −0.10, * |
| CRP (mg/L) | −0.01, NS | −0.13, *** | −0.19, *** |

(*$p < 0.05$,
**$p < 0.01$,
***$p < 0.001$).

This hypothesis was confirmed by multivariate analyses conducted among control subjects. When apo A-I was considered as the dependent variable in statistical models including IF1, known determinants were found, like cigarette smoking, alcohol consumption, physical activity, BMI, the inflammatory status or presence of a patent dyslipidemia. However, IF1 was identified as a strong positive determinant of apoA-I concentrations, contributing for 26% of the whole model (Table 2A). Table 2A displays the regression coefficients and their statistical significance in a multiple regression analyses. On the right column are given the calculated contribution of each parameter to the whole statistical model.

TABLE 2A apo A-I determinants in controls (multivariate analysis)

| Parameters | β | p |
|---|---|---|
| Dyslipemia | −0.097 | 0.001 |
| ApoB | −0.1011 | 0.02 |
| Triglycerides (log) | −0.0439 | 0.03 |
| Cigarettes/day | −0.0027 | 0.04 |
| BMI | −0.0093 | 0.001 |

TABLE 2A-continued apo A-I determinants in controls (multivariate analysis)

| Parameters | β | p |
|---|---|---|
| Alcohol | 0.0021 | 0.001 |
| CRP | 0.1207 | 0.003 |
| IF1 | 0.35 | 0.001 |

Conversely, when serum IF1 was studied as the dependent variable, three strong explanatory variables were identified: apoA-I (positive relation), triglycerides and presence of dyslipidemia (negative associations) (Table 2B).

TABLE 2B

IF1 determinants in controls (multivariate analysis)

| Parameters | β | p |
|---|---|---|
| ApoA-I | 1.116 | 0.001 |
| Triglycerides (log) | −0.333 | 0.001 |
| Dyslipemia | −0.175 | 0.03 |

Altogether, these data support the view that 1°) IF1 is strongly associated with HDL markers, appearing as an independent determinant, 2°) IF1 is negatively related with levels of triglyceride-rich lipoproteins.

Serum IF1 Levels and Cardiovascular Disease.

CVD cases differed from control subjects by an increased prevalence of classical risk factors: hypertension, diabetes, dyslipidemia, increased BMI and tobacco consumptions, lower physical activity. They also displayed higher levels of triglyceride-containing lipoproteins and lower HDL markers (not shown), Mean IF1 concentration was 0.43 (±0.13) in cases versus 0.53 (±0.15 μg/ml in controls (p<0.001).

The Odds Ratio for CVD as a function of IF1 was first studied by considering quartile ranking. As compared to the first quartile of IF1 distribution, quartiles 2, 3 and 4 displayed a regular decline of CVD risk (FIG. 3). Alternatively, IF1 was considered as a continuous variable, evidencing a linear inverse relationship between IF1 concentrations and CVD risk (not shown). In a multivariate model including classical risk factors, physical activity, smoking and alcohol habits, CRP and lipoprotein levels, IF1 remained negatively related with the CVD risk, the highest IF1 quartile being associated with a 60% reduction of CVD events (FIG. 4). This supports the hypothesis that IF1 might be an independent negative predictor of cardiovascular risk.

Furthermore, a statistical interaction appeared between IF1 levels and apo A-I or HDL-C (p<0.001). To explore this interaction, IF1 and apo A-1 concentrations were divided into tertiles and CVD risk reduction was studied, taking as reference, subjects with both low IF1 and apo A-I levels. After adjustment on an extended panel of risk factors, intermediate and high levels of apo A-I conferred a >90% risk reduction, whatever are IF1 levels. At low apo A-I concentrations, increasing IF1 induced a gradual reduction of CVD risk. This indicates that high IF1 can compensate low apo A-I in protecting against cardiovascular events. Hence, in subjects with low HDL levels, increased IF1 levels might delay catabolism of HDL particles, prolonging their atheroprotective effects.

Finally, the relationship between IF1 and the seriousness of CAD were explored, using various indices. From angiographic data, the Gensini score was calculated, assessing, for each coronary stenosis, the degree of luminal narrowing and its geographic importance. As shown in FIGS. 5 and 6, the seriousness of CAD lesions gradually decreased as a function of IF1 levels. The left ventricular ejection fraction (LVEF) was analyzed by echocardiography. A positive correlation was observed with plasma IF1 concentrations. This latter observation indicates that, among CAD subjects, the myocardial function is less altered in those with high levels of plasma IF1.

In conclusion, IF1 is a new independent determinant of apo A-I and HDL-cholesterol levels. Moreover, a negative independent association was found between plasma IF1 and occurrence of CVD and with the seriousness of the disease. Assessing plasma IF1 will help to document the cardiovascular risk profile, particularly in those subjects with low levels apolipoprotein A-I and/or HDL-cholesterol.

REFERENCES

Throughout this application, various references describe the state of the art to which the invention pertains. The disclosures of these references are hereby incorporated by reference into the present disclosure.

de Andrade F M, Silveira F R, Arsand M, et al. Association between −250G/A polymorphism of the hepatic lipase gene promoter and coronary artery disease and HDL-C levels in a Southern Brazilian population. Clin Genet. May 2004; 65(5):390-395.

Baroni M G, Berni A, Romeo S, et al. Genetic study of common variants at the Apo E, Apo AI, Apo CHI, Apo B, lipoprotein lipase (LPL) and hepatic lipase (LIPC) genes and coronary artery disease (CAD): variation in LIPC gene associates with clinical outcomes in subjects with established CAD. BMC Med Genet. Sep. 10, 2003; 4:8.

Barter P, Gotto A M, LaRosa J C, et al. HDL cholesterol, very low levels of LDL cholesterol, and cardiovascular events. N Engl J Med. Sep. 27, 2007; 357(13):1301-1310).

Blom D, Yamin T T, Champy M F, et al. Altered lipoprotein metabolism in P2Y(13) knockout mice. Biochim Biophys Acta. December 2010; 1801(12):1349-1360.

Burwick N R, Wahl M L, Fang J, et al. An Inhibitor of the F1 subunit of ATP synthase (IF1) modulates the activity of angiostatin on the endothelial cell surface. J Biol Chem. Jan. 21, 2005; 280(3):1740-1745.

Cabezon E, Montgomery M G, Leslie A G, Walker J E. The structure of bovine F I-ATPase in complex with its regulatory protein IF1. Nat Struct Biol. September 2003; 10(9):744-750.

Calabresi L, Gomaraschi M, Franceschini G. Endothelial protection by high-density lipoproteins: from bench to bedside. Arterioscler Thromb Vasc Biol. Oct. 1, 2003; 23(10):1724-1731.

Castelli W P, Anderson K, Wilson P W, Levy D. Lipids and risk of coronary heart disease: The Framingham Study. Ann Epidemiol. 1992; 2: 23-28.

Chen W, Srinivasan S R, Boerwinkle E, Berenson G S. Hepatic lipase promoter C-514T polymorphism influences serial changes in HDL cholesterol levels since childhood: the Bogalusa Heart Study. Atherosclerosis. July 2003; 169(1):175-182.

Colas et al. (1996). Nature, 380, 548-50.

Cole et al., 1985, In Monoclonal Antibodies and Cancer Therapy (Alan Liss, Inc.) pp. 77-96.

Contessi S, Comelli M, Cmet S, Lippe G, Mavelli I (2007) IF(1) distribution in HepG2 cells in relation to ecto-F(0)F(1) ATPsynthase and calmodulin. J Bioenerg Biomembr 39: 291-300.

Cortes-Hernandez P, Dominguez-Ramirez L, Estrada-Bernal A, Montes-Sanchez D G, Cortes-Hernandez P, Dominguez-Ramirez L, Estrada-Bernal A, et al. The inhibitor protein of the F1F0-ATP synthase is associated to the external surface of endothelial cells. Biochem Biophys Res Commun. May 13, 2005; 330(3):844-849.

Cote et al Proc Natl Acad Sci USA. 1983; 80(7):2026-30.

Fabre A C, Malaval C, Ben Addi A, et al. P2Y13 receptor is critical for reverse cholesterol transport. Hepatology. October 2010; 52(4):1477-1483.

Desrumaux C et al. Arterioscler Thromb Vasc Biol 1999; 19:266-75

Garber D W, Datta G, Chaddha M, et al. A new synthetic class A amphipathic peptide analogue protects mice from diet-induced atherosclerosis. J Lipid Res. April 2001; 42(4):545-552.

Gensini G G. A more meaningful scoring system for determining the severity of coronary heart disease. Am J Cardiol. February 1983; 51(3):606.

Giorgio V, Bisetto E, Franca R, Harris D A, Passamonti S, et al. (2010) The ectopic F(O)F(1) ATP synthase of rat liver is modulated in acute cholestasis by the inhibitor protein IF1. J Bioenerg Biomembr 42: 117-123.

Giorgio V, Bisetto E, Franca R, Harris D A, Passamonti S, Lippe G. The ectopic F(O)F(1) ATP synthase of rat liver is modulated in acute cholestasis by the inhibitor protein IF1. J Bioenerg Biomembr. April 2010; 42(2):117-123.

Gordon D J, Rifkind B M. High-density lipoprotein: the clinical implications of recent studies. N Engl J Med. 1989; 321: 1311-1316.

Grarup N, Andreasen C H, Andersen M K, et al. The −2500>A promoter variant in hepatic lipase associates with elevated fasting serum high-density lipoprotein cholesterol modulated by interaction with physical activity in a study of 16,156 Danish subjects. J Clin Endocrinol Metab. June 2008; 93(6):2294-2299.

Green D W, Grover G J. The IF(1) inhibitor protein of the mitochondrial (F(1)F(0)-ATPase. Biochim Biophys Acta. May 31, 2000; 1458(2-3):343-355.

Ho Hong S, Rhyne J, Zeller K, Miller M. Novel ABCA1 compound variant associated with HDL cholesterol deficiency. Biochim Biophys Acta. May 21, 2002; 1587(1): 60-64.

Ichikawa N, Ushida S, Kawabata M, Masazumi Y. Nucleotide sequence of cDNA coding the mitochondrial precursor protein of the ATPase inhibitor from humans. Biosci Biotechnol Biochem. December 1999; 63(12):2225-2227.

Ishii J, Nagano M, Kujiraoka T, et al. Clinical variant of Tangier disease in Japan: mutation of the ABCA1 gene in hypoalphalipoproteinemia with corneal lipidosis. J Hum Genet. 2002; 47(7):366-369

Jacquet S, Malaval C, Martinez L O, et al. The nucleotide receptor P2Y13 is a key regulator of hepatic high-density lipoprotein (HDL) endocytosis. Cell Mol Life Sci. November 2005; 62(21):2508-2515.

Jackson et al., 1988 FEBS Lett. 229: 224

Jayasena (1999) Clin Chem. 45(9):1628-50.

Kohler et al. Nature. 1975; 256(5517):495-7.

Mangiullo R, Gnoni A, Leone A, Gnoni G V, Papa S, Zanotti F. Structural and functional characterization of F(o)F(1)-ATP synthase on the extracellular surface of rat hepatocytes. Biochim Biophys Acta. October 2008; 1777(10): 1326-1335.

Martinez L O, Jacquet S, Esteve J P, et al. Ectopic beta-chain of ATP synthase is an apolipoprotein A-1 receptor in hepatic HDL endocytosis. Nature. Jan. 2, 2003; 421 (6918):75-79.

Mimura et al., 1993 J. Biochem. 113: 350

Navab M, Anantharamaiah G M, Reddy S T, et al. Apolipoprotein A-I mimetic peptides. Arterioscler Thromb Vase Biol. July 2005; 25(7):1325-1331.

Navab M, Anantharamaiah G M, Reddy S T, et al. Oral D-4F causes formation of pre-beta high-density lipoprotein and improves high-density lipoprotein-mediated cholesterol efflux and reverse cholesterol transport from macrophages in apolipoprotein E-null mice. Circulation. Jun. 29, 2004; 109(25):3215-3220.

Navab M, Anantharamaiah G M, Reddy S T, Fogelman A M. Apolipoprotein A-1 mimetic peptides and their role in atherosclerosis prevention. Nat Clin Pract Cardiovasc Med. October 2006; 3(10):540-547.

Nissen S E, Tsunoda T, Tuzcu E M, et al. Effect of recombinan ApoA-I Milano on coronary atherosclerosis in patients with acute coronary syndromes: a randomized controlled trial. Jama. Nov. 5, 2003; 290(17):2292-2300.

Lebowitz et al. 1993 Arch. Biochem, Biophys. 301: 64.

Oka T et al. J Lipid Res 2000; 41:1651

Pullman M E, Monroy G C. A Naturally Occurring Inhibitor of Mitochondrial Adenosine Triphosphatase. J Biol Chem. November 1963; 238:3762-3769. Solaini et al., 1997 Biochem J. 327: 443.

Schmidt C, Lepsverdize E, Chi S L, et al. Amyloid precursor protein and amyloid beta-peptide bind to ATP synthase and regulate its activity at the surface of neural cells. Mol Psychiatry. October 2008; 13(10):953-969.

Teran-Garcia M, Santoro N, Rankinen T, et al. Hepatic lipase gene variant −514C>T is associated with lipoprotein and insulin sensitivity response to regular exercise: the HERITAGE Family Study. Diabetes. July 2005; 54(7):2251-2255.

Tuerk et al. (1990) Science, 249, 505-510 van Raaij M J, Orriss G L, Montgomery M G, et al. The ATPase inhibitor protein from bovine heart mitochondria: the minimal inhibitory sequence. Biochemistry. 1996; 35(49):15618-15625.

von Eckardstein A, Hersberger M, Rohrer L. Current understanding of the metabolism and biological actions of HDL. Curr Opin Clin Nutr Metab Care. March 2005; 8(2):147-152

Waksman R, Torguson R, Kent K M, et al. A first-in-man, randomized, placebo-controlled study to evaluate the safety and feasibility of autologous delipidated high-density lipoprotein plasma infusions in patients with acute coronary syndrome. J Am Coll Cardiol. Jun. 15, 2010; 55(24):2727-2735.

Wang J, Burnett J R, Near S, et al. Common and rare ABCA1 variants affecting plasma HDL cholesterol. Arterioscler Thromb Vase Biol. August 2000; 20(8):1983-1989.

Yamakawa-Kobayashi K, Yanagi H, Yu Y, Endo K, Arinami T, Hamaguchi H. Associations between scrum high-density lipoprotein cholesterol or apolipoprotein AI levels and common genetic variants of the ABCA1 gene in Japanese school-aged children. Metabolism. February 2004; 53(2): 182-186.

Zentella-Dehesa A, et al. (2005) The inhibitor protein of the F1F0-ATP synthase is associated to the external surface of endothelial cells. Biochem Biophys Res Commun 330: 844-849.

Su Z, Zhang S, Nebert D W, et al. A novel allele in the promoter of the hepatic lipase is associated with increased concentration of HDL-C and decreased promoter activity. J Lipid Res. October 2002; 43(10):1595-1601.

The invention claimed is:

1. A method for measuring the level of circulating inhibitory factor 1 (IF1) protein in a subject comprising the step of
    a) contacting a blood sample or a cerebrospinal fluid sample obtained from said patient with a binding partner capable of selectively interacting with IF1 to allow formation of a binding partner-IF1 complex; and
    b) measuring the level of circulating IF1 protein,
    wherein said binding partner is an antibody or an aptamer.

2. The method according to claim 1 further comprising, between step a) and step b), the steps of:
    separating any unbound material of the blood sample or the cerebrospinal fluid sample from the binding partner-IF1 complex,
    contacting the binding partner-IF1 complex with a labeled secondary binding molecule,
    separating any unbound secondary binding molecule from secondary binding molecule-IF1 complexes and
    detecting the secondary binding molecule of the secondary binding molecule-IF1 complexes.

3. The method according to claim 1 wherein said blood sample or cerebrospinal fluid sample is treated prior to step a) so as to remove the cell fraction from the sample.

4. A method for measuring the level of circulating inhibitory factor 1 (IF1) protein in a subject comprising the step of
    measuring the level of circulating IF1 protein in a blood sample or a cerebrospinal fluid sample obtained from said subject.

5. The method according to claim 4 wherein said blood sample or cerebrospinal fluid sample is firstly treated so as to remove the cell fraction from the sample.

* * * * *